(12) United States Patent
Schottek et al.

(10) Patent No.: US 6,600,066 B1
(45) Date of Patent: Jul. 29, 2003

(54) METHOD FOR PRODUCING MONO-ORGANOBORANES OR DI-ORGANOBORANES

(75) Inventors: Jörg Schottek, Frankfurt (DE); Patricia Becker, Mörfelden-Walldorf (DE); Iris Küllmer, Frankfurt (DE)

(73) Assignee: Basell Polyolefine GmbH, Wesseling (DE)

( * ) Notice: Subject to any disclaimer, the term of this patent is extended or adjusted under 35 U.S.C. 154(b) by 0 days.

(21) Appl. No.: 09/868,074

(22) PCT Filed: Dec. 17, 1999

(86) PCT No.: PCT/EP99/10032

§ 371 (c)(1), (2), (4) Date: Jun. 14, 2001

(87) PCT Pub. No.: WO00/37476

PCT Pub. Date: Jun. 29, 2000

(30) Foreign Application Priority Data

Dec. 19, 1998 (DE) .......................... 198 58 829

(51) Int. Cl.[7] .............. C07F 5/02; C07F 5/04
(52) U.S. Cl. .............. 562/7; 564/9; 558/298
(58) Field of Search .................. 558/286, 298; 562/7; 564/8, 9

(56) References Cited

U.S. PATENT DOCUMENTS 3,090,801 A * 5/1963 Washburn

OTHER PUBLICATIONS

Journal of Chemistry– London Chambers and Chivers pp. 3933–3930 1965.*

Chem abs 68:59640 abs of Chem Ber 101(1) pp. 291–294 by Schmidt et al 1968.*

Chem abs 102:62298 abs of J Org Chem by Domaille et al 50(2) pp. 189–194 1985.*

Beilstein BRN 3102103 abs or J Organomet Chem by Chivers 13, pp. 177–186 1968.*

Beilstein BRN 3096669 abs of J Organomet Chem 13 pp. 177–186 1968.*

J.Am.Chem.Soc., 77, 1955, 2491–2494, Letsinger et al.

J.Am.Chem.Soc.,80,1958,5409–5411,Povlock et al.

Chem.Abst.vol. 93,No.9, PL 105929.

Advan.Chem.Ser.,32,208–220, Washburn et al.

J.Chem.Soc., 1965, 3933–3939,Chambers et al.

J.Chem.Soc., Dalton Trans, 1996,255–270, Bochmann.

* cited by examiner

Primary Examiner—Jean F. Vollano
(74) Attorney, Agent, or Firm—Keil & Weinkauf

(57) ABSTRACT

A novel process for preparing perhalogenated monoorganoboranes or diorganoboranes which makes it possible to obtain these compounds under conditions which can readily be implemented in the industry is described.

5 Claims, No Drawings

METHOD FOR PRODUCING MONO-ORGANOBORANES OR DI-ORGANOBORANES

This is a 371 of PCT/EP99/10032 filed Dec. 17, 1999, now WO 00/37476.

The present invention relates to a novel process for preparing perhalogenated monoorganoboranes or diorganoboranes, which makes it possible to obtain these compounds under conditions which can readily be implemented in industry.

Various methods of preparing diorganohydroxyboranes are described in the prior art. Thus, Davidson et al. describe the preparation of diorganohydroxyboranes from dioxyorganoboranes using Grignard compounds (J. M. Davidson et al., French Soc, 1960, 191). The preparation of diorganohydroxyboranes from Lewis base-diorganooxyboranes is likewise known. For this purpose, diarylhydroxyborane compounds with 2-aminoethanol are prepared as salts with the aid of aqueous mineral acids. Acid hydrolysis gives the desired diorganohydroxyboranes (R. L. Letsinger, I. Skoog, J. Am. Chem. Soc., 77, 1955, 2491).

Thus, for example, reaction of trimethoxyboroxins with 2 equivalents of phenylmagnesium bromide and subsequently with ethanolamine gives (2-aminoethoxy)bis(phenyl)borane from which the corresponding diphenylhydroxyborane is synthesized as described (T. P. Povlock, W. T. Lippincott, J. Am. Chem. Soc., 80, 1958, 5409). Triorganooxyboranes react with 2 equivalents of Grignard compound and subsequent hydrolysis to give the desired diorganbhydroxyboranes (R. M. Washburn, F. A. Billig, M. Bloom, C. F. Albright, E. Levens, Advan. Chem. Ser., 32, 208, 1961).

Partially halogenated or perhalogenated diphenylhydroxyboranes have hitherto not been obtainable via these routes. Thus, di(pentafluorophenyl)hydroxyborane can be prepared by hydrolysis of di(pentafluorophenyl)chloroborane in acetone (R. D. Chambers, T. Chivers, J. Chem. Soc., 1965, 3933). The preparation of di(pentafluorophenyl)chloroborane is carried out by reacting dimethylbis(pentafluorophenyl)tin with boron trichloride under superatmospheric pressure in a bomb tube and can therefore not be employed in this form in industry. In addition, the yields of di(pentafluorophenyl)chloroborane, which is used as precursor for preparing di(pentafluorophenyl)hydroxyborane, obtained in this process are extremely low at only 36% (R. D. Chambers, T. Chivers, J. Chem. Soc., 1965, 3933). The synthesis of di(pentafluorophenyl)hydroxyborane from di(pentafluorphenyl)chloroborane in acetone using stoichiometric amounts of water is likewise unsatisfactory, giving a yield of only 49%.

Organoboron compounds are effective cocatalysts in the polymerization of olefins using metallocenes (M. Bochmann, J. Chem. Soc., Dalton Trans, 1996, 255–270). Partially halogenated or perhalogenated diorganohydroxyboranes in particular serve as precursors for preparing appropriate cocatalysts.

For this reason, there is a great need for a simple process for preparing the compounds mentioned at the outset, which process can, firstly, be carried out on an industrial scale while avoiding the formation of stannane compounds in the preparation and, secondly, provides the target compound in good yields.

We have now surprisingly found that organohaloarylborane compounds can be converted into the corresponding diorganohydroxy compounds in virtually quantitative yield by hydrolysis at elevated temperatures.

The present invention provides a process for preparing compounds of the formula (I)

$(C_6R^1{}_5)_{1+l}M(XR^9{}_p)_{2-l}$ (I)

where

R$_1$ are identical or different and are each, independently of one another, a hydrogen atom, a halogen atom or a $C_1$–$C_{20}$ group such as $C_1$–$C_{20}$-alkyl, $C_6$–$C_{14}$-aryl, $C_1$–$C_{10}$-alkoxy, $C_2$–$C_{10}$-alkenyl, $C_7$–$C_{20}$-arylalkyl, $C_7$–$C_{20}$-alkylaryl, $C_6$–$C_{10}$-aryloxy, $C_1$–$C_{10}$-haloalkyl, $C_6$–$C_{10}$-haloaryl, $C_2$–$C_{10}$-alkynyl or $C_3$–$C_{20}$-alkylsilyl, M is an element of main group III of the Periodic Table of the Elements, preferably aluminum or boron, very particularly preferably boron, X are identical or different and are each, independently of one another, an element of main group V or VI of the Periodic Table of the Elements, preferably oxygen or nitrogen, R$^9$ is a hydrogen atom or a $C_1$–$C_{20}$ group such as $C_1$–$C_{20}$-alkyl or $C_6$–$C_{14}$-aryl, p is 1 or 2, l is 0 or 1, by reacting a compound of the formula (II)

$(C_6R^1{}_5)_{1+n}M^1R^2{}_{2-n}$ (II)

where

R$^1$ is as defined under formula (I),

M$^1$ is an element of main group III of the Periodic Table of the Elements, preferably aluminum or boron, very particularly preferably boron, R$^2$ are identical or different and are each, independently of one another, a hydrogen atom, a halogen atom or a $C_1$–$C_{20}$ group such as $C_1$–$C_{20}$-alkyl, $C_6$–$C_{14}$-aryl or $C_6$–$C_{14}$-haloaryl, particularly preferably a $C_6$–$C_8$-fluoroaryl group, very particularly preferably a perfluorinated phenyl ring and n is an integer from 0 to 2 with a compound of the formula (III)

$B^1R^3R^4$ (III)

where

R$^3$,R$^4$ are identical or different and are each, independently of one another, a hydrogen atom, a halogen atom, a $C_1$–$C_{20}$ group such as $C_1$–$C_{20}$-alkyl, $C_6$–$C_{14}$-aryl, $C_1$–$C_{10}$-alkoxy, $C_2$–$C_{10}$-alkenyl, $C_7$–$C_{20}$-arylalkyl, $C_7$–$C_{20}$-alkylaryl, $C_6$–$C_{10}$-aryloxy, $C_1$–$C_{10}$-haloalkyl, $C_6$–$C_{10}$-haloaryl, $C_2$–$C_{10}$-alkynyl, $C_3$–$C_{20}$-alkylsilyl, an —OR$^6{}_2$ group, where R$^6$ is a $C_1$–$C_{20}$ group such as $C_1$–$C_{20}$-alkyl or $C_6$–$C_{14}$-aryl, or one or more radicals R$^3$, R$^4$ form an —NR$^7{}_2$ group, where R$^7$ is a hydrogen atom, a halogen atom or a $C_1$–$C_{20}$ group such as $C_1$–$C_{20}$-alkyl or $C_6$–$C_{14}$-aryl, B$^1$ is an element of main group V or VI of the Periodic Table of the Elements, preferably oxygen or nitrogen, particularly preferably oxygen, or alternatively or additionally with an inorganic salt of the formula (IV),

$Z_j(VY_h)_i*B^1R^3R^4$ (IV)

where

R$^3$,R$^4$ are each a hydrogen atom,

B$^1$ is an element of main group V or VI of the Periodic Table of the Elements, preferably oxygen or nitrogen, particularly preferably oxygen, Z can be an element of main group I, II, III or IV or an element of transition groups I–VIII, or a mixture of elements from these groups, or is ($NH_4$), V is an element of main group IV, V, VI or VII or an element of transition groups I–VIII, Y is an element of main group IV, V, VI or VII or an element of transition groups I–VIII, j, h, i are each a number in the range from 0 to 1000, at a temperature above room temperature, to form the compound of the formula (I).

The product of the formula (I) formed can, if desired, be worked up further by appropriate means. This can be achieved, for example, by extraction of the compound (I) using aprotic, aliphatic and/or aromatic hydrocarbons, with any solid residues being able to be separated off.

After extraction, the extractant is separated off and, depending on the purity desired, further purification of the compound of the formula (I) can be carried out.

Preferred, nonlimiting examples of compounds of the formula (III) are water and/or alcohols such as methanol, ethanol, propanol or butanol, and also mixtures of these.

Preferred, nonlimiting examples of compounds of the formula (IV) are $AlCl_3*6H_2O$, $Al(NO_3)_3*9H_2O$, $Al_2(SO_4)_3*18H_2O$, $NH_4Cr(SO_4)_2*12H_2O$, $(NH_4)_2Fe(SO_4)_3*6H_2O$, $(NH_4)_2Fe(SO_4)_3*12H_2O$, $NH_4MgPO_4*6H_2O$, $(NH_4)_2SO_3*H_2O$, $(NH_4)W_7O_{24}*6H_2O$, $BaBr_2*2H_2O$, $Ba(ClO_3)_2O$, $Ba(NO_2)_2*H_2O$, $Cr(NO_3)_3*6H_2O$, $Cr_2(SO_4)_3*18H_2O$, $Na_2HPO_4*12H_2O$, $Fe(NO_3)_3*9H_2O$, $FeSO_4*7H_2O$, $CdCl_2*2.5H_2O$, $KAl(SO_4)_2*12H_2O$, $K_4[Fe(CN)_6]*3H_2O$, $CuCl_2*2H_2O$, $Cu(NO_3)_2*3H_2O$, $Mg(NO_3)_2*6H_2O$, $MgSO_4*7H_2O$, $Na_2SO_3*7H_2O$, $NiSO_4*7H_2O$, and mixtures of these.

The process of the present invention makes it possible to obtain, in particular, the compounds bis(pentafluorophenyl) hydroxyborane, di(phenyl)hydroxyborane, di(o-tolyl) hydroxyborane, di(p-anisyl)hydroxyborane, di(nonafluorobiphenyl)hydroxyborane, di(trifluoromethyl) phenylhydroxyborane, di(p-biphenyl)hydroxyborane, di(p-chlorophenyl)hydroxyborane, di(p-fluoro-1-naphthyl) phenylhydroxyborane or pentafluorophenyldihydroxyborane in industrial quantities.

The way in which the process of the present invention is carried out is described in more detail below:

Firstly, one or more compounds of the formula (II) are placed in a reaction vessel. The compounds can either be dissolved or suspended in a solvent or be present as such. Solvents which can be employed are aliphatic or aromatic hydrocarbons such as n-pentane, isopentane, n-hexane, n-heptane, cyclohexane, isododecane, n-octane, n-nonane, n-decane, petroleum ether, toluene, benzene, o-xylene, m-xylene, p-xylene, 1,2,3-trimethylbenzene, 1,2,4-trimethylbenzene, 1,2,5-trimethylbenzene, 1,3,5-trimethylbenzene, ethylbenzene, propylbenzene, etc., and also mixtures of these. The compound(s) is/are placed in the reaction vessel at from −100° C. to 300° C., preferably from −80° C. to 200° C., particularly preferably from 0° C. to 150° C. The compound of the formula (II) is advantageously present in a liquid phase.

Subsequently, one or more compounds of the formula (III), for example water and/or alcohols, and/or the compound (IV), e.g. an inorganic salt, in which the compound of the formula (III) is present in bound form is/are added. These can likewise be dissolved or suspended in a solvent or can be added as such. Solvents which can be employed are those described above; preference is given to using the same solvent. The addition is carried out over a period of from 1 minute to 96 hours. It is preferably carried out over a period of from 10 minutes to 8 hours. The temperature of the initial charge during the addition is from −100° C. to 200° C., preferably from −80° C. to 40° C., particularly preferably from 0° C. to 150° C. The temperature is selected so that at least one reactant is present in a liquid phase. Furthermore, the reaction may be carried out at atmospheric pressure, but can also be carried out at superatmospheric pressure, although this requires appropriate reactors. Depending on the physical properties of the compound of the formula (II), cooling is carried out by means of a low-temperature cooler which may be operated using refrigerants.

In the process of the present invention, the addition of the compound of the formula (III) and/or (IV) to the compound of the formula (II) can be carried out quantitatively right at the beginning, with the mixture subsequently being heated to a temperature of above room temperature. If the initial charge is at a temperature above room temperature when the compound of the formula (III) and/or (IV) is added to the compound of the formula (II), the reaction commences with the addition. To complete the reaction, the temperature can be increased further and/or an appropriate further amount of the compound of the formula (III) and/or (IV) can be added to the compound of the formula (II). The order of the addition of the compound of the formula (III) and/or (IV) to the compound of the formula (II) and subsequent heating is not of critical importance. Depending on the reactivity of the compound of the formula (II), the compound of the formula (III) and/or (IV) can be added to the previously heated initial charge comprising the compound of the formula (II).

The stoichiometric ratio of compounds of the formula (II) to compounds of the formula (III) and/or (IV) is in the range from 1:1000 to 100:1. Particular preference is given to a stoichio-metric ratio of compounds of the formula (II) to compounds of the formula (III) of from 1:100 to 1:1; particular preference is given to 1:1.2 for the compound of the formula (III) and to 1:1.7 for compounds of the formula (IV), based on bound water.

The reaction temperature is above room temperature (20° C.), preferably from 30° C. to 200° C., particularly preferably from 40° C. to 180° C., in particular from 50° C. to 170° C.

At least one reactant is preferably present in a liquid phase. The reaction is particularly preferably carried out under reflux. It is also advantageous for the bath temperature of the heating bath to be in the range from 50° C. to 200° C., so that the reaction time is considerably shortened. The reaction time is, depending on the reaction temperature selected, in the range from 1 minute to 96 hours. Preference is given to a reaction time of from 10 minutes to 8 hours.

The extractants used for working up the reaction mixture are aprotic, aliphatic or aromatic hydrocarbons or mixtures thereof; the extraction can serve to separate any by-products formed from the target compound of the formula (I). Suitable extractants are, for example, n-pentane, isopentane, n-hexane, n-heptane, cyclohexane, isododecane, n-octane, n-nonane, n-decane, petroleum ether, toluene, benzene, o-xylene, m-xylene, p-xylene, 1,2,3-trimethylbenzene, 1,2,4-trimethylbenzene, 1,2,5-trimethylbenzene, 1,3,5-trimethylbenzene, ethylbenzene, propylbenzene and mixtures of these. When using compounds of the formula (IV), it may be necessary to carry out an additional filtration step in order to remove the inorganic decomposition products from the reaction mixture.

The previously purified compound of the formula (I) can, depending on the purity required, be purified further by means of known techniques, e.g. distillation, recrystallization, extraction or sublimation.

The invention is illustrated by the following, nonlimiting examples.

General procedures: Preparation and handling of the compounds were carried out in the absence of air and moisture under argon (Schlenk technique). All solvents required were dried by boiling for a number of hours over suitable desiccants and subsequent distillation under argon before use.

EXAMPLE 1

Variant A for Preparing bis(pentafluorophenyl) hydroxyborane a) Synthesis of tris(pentafluorophenyl)borane×3H$_2$O (1)

20 g (39 mmol) of tris(pentafluorophenyl)borane are suspended in 150 ml of pentane and, under reflux, a solution of 1.8 ml (97.5 mmol) of water in 40 ml of toluene is then added over a period of 30 minutes. The mixture is subsequently stirred for another two hours under reflux. The solution is subsequently cooled to 0° C. Over a period of 20 minutes, the product precipitates as a white solid. The product is isolated and dried in an oil pump vacuum. This gives 20.5 g (91%) of colorless tris(pentafluorophenyl)borane×3H$_2$O. $^1$H-NMR(C$_6$D$_6$, 400 MHZ): −135.0 (m, 6 F, o-B(C$_6$F$_5$)$_2$), −154.5 (m, 3 F, p-B(C$_6$F$_5$)$_2$), −162.5 (m, 6 F, m-B(C$_6$F$_5$)$_2$) ppm.

b) Synthesis of bis(pentafluorophenyl)hydroxyborane 20.5 g (36 mmol) of the tris(pentafluorophenyl)borane× 3H$_{2O}$ adduct (1) prepared under a) are dissolved in 150 ml of toluene and refluxed for 2.5 hours. After this time, the solvent is taken off in an oil pump vacuum. The residue is subsequently dried in an oil pump vacuum and does not have to be purified further. This gives 8.7 g (67%) of colorless bis(pentafluorophenyl)hydroxyborane. The boroxin content is 10%. $^1$H-NMR(C$_6$D$_6$, 400 MHz): −133.1 (m, 4 F, o-B (C$_6$F$_5$)$_2$), −147.9 (m, 2 F, p-B(C$_6$F$_5$)$_2$), −161.1 (m, 4 F, m-B(C$_6$F$_5$)$_2$) ppm.

EXAMPLE 2

Variant B for Preparing bis(pentafluorophenyl) hydroxyborane 20 g (39 mmol) of tris(pentafluorophenyl)borane are suspended in 150 ml of heptane and, under reflux, a solution of 1.8 ml (97.5 mmol) of water in 40 ml of toluene is then added over a period of 30 minutes. The mixture is subsequently stirred for another five hours under reflux. The solution is subsequently cooled to 0° C. Over a period of 30 minutes, the product precipitates as a white solid. The product is isolated and washed three times with 50 ml each time of pentane and subsequently dried in an oil pump vacuum. This gives 11.5 g (80%) of colorless bis (pentafluorophenyl)hydroxyborane. The boroxin content is 10%. $^1$H-NMR(C$_6$D$_6$, 400 MHz): −133.1 (m, 4 F, o-B(C$_6$F$_5$)$_2$), −147.9 (m, 2 F, p-B(C$_6$F$_5$)$_2$), −161.1 (m, 4 F, m-B(C$_6$F$_5$)$_2$) ppm.

EXAMPLE 3

Variant C for Preparing bis(pentafluorophenyl) hydroxyborane 20 g (39 mmol) of tris(pentafluorophenyl)borane together with 150 ml of toluene are placed in a reaction vessel and the mixture is subsequently heated 100° C. 1.8 ml (97.5 mmol) of water in 40 ml of toluene are subsequently added dropwise to this solution over a period of 30 minutes. The mixture is subsequently stirred for another two hours at 100° C. After this time, the solvent is taken off in an oil pump vacuum. The residue does not have to be purified further. This gives 12.6 g (89%) of colorless bis(pentafluorophenyl) hydroxyborane. The boroxin content is 5%. $^1$H-NMR(C$_6$D$_6$, 400 MHz): −133.1 (m, 4 F, o-B(C$_6$F$_5$)$_2$), −147.9 (m, 2 F, p-B(C$_6$F$_5$)$_2$), −161.1 (m, 4 F, m-B(C$_6$F$_5$)$_2$) ppm.

EXAMPLE 4

Variant D for Preparing bis(pentafluorophenyl) hydroxyborane (using an inorganic salt)

676.9 q of a toluene solution of tris(pentafluorophenyl) borane (10.4% strength by weight=70.37 g) are admixed with 8.8 g of aluminum sulfate octadecahydrate which has been ground in a mortar and the mixture is stirred under reflux for 15.5 hours. The insoluble aluminum sulfate is separated off from the hot reaction solution and the solvent of the filtrate is removed in an oil pump vacuum. The residue is taken up in 700 ml of toluene, stirred at room temperature for 30 minutes and the insoluble residue is subsequently separated off on a G4 frit. The solvent of the filtrate is removed in an oil pump vacuum. The now brown residue is taken up in 200 ml of heptane and stirred for another one hour. The mixture is subsequently filtered and the residude obtained is washed with 2×30 ml of heptane. The white solid remaining on the G4 frit is dried in an oil pump vacuum. This gives 45.6 g (91%) of bis(pentafluorophenyl)borinic acid.

The boroxin content is less than 1%. $^1$H-NMR(C$_6$D$_6$, 400 MHZ): −133.1 (m, 4 F, o-B(C$_6$F$_5$)$_2$), −147.9 (m, 2 F, p-B(C$_6$F$_5$)$_2$), −161.1 (m, 4 F, m-B(C$_6$F$_5$)$_2$) ppm.

We claim:

1. A process for preparing a compound of formula (I)

where

R$^1$ are identical or different radicals which are independently selected from a group consisting of hydrogen, halogen, C$_1$–C$_{20}$-alkyl, C$_6$–C$_{14}$-aryl, C$_1$–C$_{10}$-alkoxy, C$_2$–C$_{10}$-alkenyl, C$_7$–C$_{20}$-arylalkyl, C$_7$–C$_{20}$-alkylaryl, C$_6$–C$_{10}$-aryloxy, C$_1$–C$_{10}$-haloalkyl, C$_6$–C$_{10}$-haloaryl, C$_2$–C$_{10}$-alkynyl and C$_3$–C$_{20}$-alkylsilyl, M is boron, X are identical or different elements which are independently selected from a group consisting of elements of main group VI of the Periodic Table of the Elements, R$^9$ is hydrogen, C$_1$–C$_{20}$-alkyl or C$_6$–C$_{14}$-aryl, p is 1 or 2, l is 0 or 1, which comprises reacting a compound of formula (II)

where

M$^1$ is boron,

R$^2$ are perfluorinated phenyl rings, and n is an integer from 0 to 2, with a compound of formula (III)

where

R$^3$, R$^4$ are identical or different radicals which are independently selected from a group consisting of hydrogen, halogen, $C_1$–$C_{20}$-alkyl, $C_6$–$C_{14}$-aryl, $C_1$–$C_{10}$-alkoxy, $C_2$–$C_{10}$-alkenyl, $C_7$–$C_{20}$-arylalkyl, $C_7$–$C_{20}$-alkylaryl, $C_6$–$C_{10}$-aryloxy, $C_1$–$C_{10}$-haloalkyl, $C_6$–$C_{10}$-haloaryl, $C_2$–$C_{10}$-alkynyl, $C_3$–$C_{20}$-alkylsilyl, —$OR^6{}_2$ groups, where $R^6$ is $C_1$–$C_{20}$-alkyl or $C_6$–$C_{14}$-aryl, and —$NR^7{}_2$ groups, where $R^7$ is a hydrogen atom, a halogen atom, $C_1$–$C_{20}$-alkyl or $C_6$–$C_{14}$-aryl, $B^1$ is an element of main group VI of the Periodic Table of the Elements, at a temperature above room temperature, to form the compound of formula (I).

2. The process of claim 1, wherein, in formulae (I)–(III),

X is oxygen, and $B^1$ is oxygen.

3. The process of claim 1, wherein the compound of formula (III) used is water or an alcohol or a mixture thereof.

4. The process of claim 1, wherein the reaction temperature is in the range from 30° C. to 200° C.

5. The process of claim 1, wherein the compound of formula (I) is bis(pentafluorophenyl)hydroxyborane, di(phenyl)hydroxyborane, di(o-tolyl)hydroxyborane, di(p-anisyl)hydroxyborane, di(nonafluorobiphenyl)hydroxyborane, di(trifluoromethylphenyl)hydroxyborane, di(p-biphenyl)hydroxyborane, di(-p-chlorophenyl)hydroxyborane, di(p-fluoro-1-naphthyl)phenyl- hydroxyborane or pentafluorophenyldihydroxyborane.

* * * * *